United States Patent
Dubois et al.

(10) Patent No.: US 10,125,221 B2
(45) Date of Patent: Nov. 13, 2018

(54) AMINO ACID PREPARATION METHOD COMPRISING A STEP OF HYDROFORMYLATION OF AN UNSATURATED FATTY NITRILE

(71) Applicants: ARKEMA FRANCE, Colombes (FR); CENTRE NATIONAL DE LA RECHERCHE SCIENTIFIQUE, Paris (FR); UNIVERSITE DE RENNES 1, Rennes (FR)

(72) Inventors: Jean-Luc Dubois, Millery (FR); Jean-Luc Couturier, Lyons (FR); Jean-François Carpentier, Acigne (FR); Jérémy Ternel, Chantepie (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/362,309

(22) PCT Filed: Dec. 3, 2012

(86) PCT No.: PCT/FR2012/052778
§ 371 (c)(1),
(2) Date: Jun. 2, 2014

(87) PCT Pub. No.: WO2013/079888
PCT Pub. Date: Jun. 6, 2013

(65) Prior Publication Data
US 2014/0323684 A1     Oct. 30, 2014

(30) Foreign Application Priority Data
Dec. 1, 2011     (FR) ...................... 11 61036

(51) Int. Cl.
| | |
|---|---|
| *C07C 227/26* | (2006.01) |
| *C08G 69/08* | (2006.01) |
| *C07C 227/04* | (2006.01) |
| *C07C 253/30* | (2006.01) |
| *C07C 253/22* | (2006.01) |

(52) U.S. Cl.
CPC ............ *C08G 69/08* (2013.01); *C07C 227/04* (2013.01); *C07C 227/26* (2013.01); *C07C 253/22* (2013.01); *C07C 253/30* (2013.01)

(58) Field of Classification Search
None
See application file for complete search history.

(56) References Cited

U.S. PATENT DOCUMENTS

| | | | |
|---|---|---|---|
| 4,356,333 A | 10/1982 | Yoshimura et al. | |
| 4,510,331 A | 4/1985 | Yoshimura et al. | |
| 6,307,108 B1 | 10/2001 | Argyropoulos et al. | |
| 6,680,395 B2 | 1/2004 | Springer | |
| 6,696,582 B2 | 2/2004 | Springer et al. | |
| 6,800,783 B2 | 10/2004 | Springer et al. | |
| 7,026,473 B2 | 4/2006 | Drent et al. | |
| 7,138,544 B2 | 11/2006 | Springer et al. | |
| 7,799,945 B2 | 9/2010 | Springer | |
| 2011/0224454 A1 | 9/2011 | Dubois | |
| 2011/0300590 A1 | 12/2011 | Dubois | |
| 2012/0035393 A1 | 2/2012 | Weber et al. | |
| 2013/0345388 A1 | 12/2013 | Brandhorst et al. | |
| 2014/0148607 A1 | 5/2014 | Dubois | |

FOREIGN PATENT DOCUMENTS

| | | |
|---|---|---|
| DE | 31 12 213 A1 | 1/1982 |
| FR | 2 769 624 A1 | 4/1999 |
| FR | 2 970 253 A1 | 7/2012 |
| FR | 2 978 147 A1 | 1/2013 |
| FR | 2 979 342 A1 | 3/2013 |
| GB | 641 955 A | 8/1950 |
| GB | 2 074 156 A | 10/1981 |
| WO | WO 97/33854 A1 | 9/1997 |
| WO | WO 2010/055273 A1 | 5/2010 |
| WO | WO 2010/089512 A1 | 8/2010 |
| WO | WO 2010/108586 A1 | 9/2010 |

OTHER PUBLICATIONS

Miller et al. Journal of the American Oil Chemists' Society, 1974, 51(10), 427-32.*
International Search Report (PCT/ISA/210) dated Feb. 4, 2013, by the French Patent Office as the International Searching Authority for International Application No. PCT/FR2012/052778.

* cited by examiner

*Primary Examiner* — Ana Z Muresan
(74) *Attorney, Agent, or Firm* — Buchanan Ingersoll & Rooney P.C.

(57) ABSTRACT

A process for synthesizing an ω-amino acid compound of formula $$HOOC-(CH_2)_{r+2}-CH_2NH_2,$$

wherein 4≤r≤13 from a monounsaturated fatty nitrile compound of formula $$CH_2=CH-(CH_2)_r-CN$$

the process comprising: 1) a step of hydroformylation of the mono unsaturated fatty nitrile compound by reacting said nitrile with carbon monoxide and di hydrogen 5e-a5 to obtain a nitrile aldehyde compound of formula HOC—(CH2)r+2-CN, then 2) a step of oxidation, in the presence of dioxygen, of the nitrile aldehyde compound to obtain a corresponding nitrile acid compound of formula HOOC—(CH2)r+2-CN, and 3) a step of reduction of the nitrile acid compound to give an w-amino acid of formula $$HOOC-(CH_2)_{r+2}-CH_2NH_2.$$

22 Claims, No Drawings

AMINO ACID PREPARATION METHOD COMPRISING A STEP OF HYDROFORMYLATION OF AN UNSATURATED FATTY NITRILE

The work which led to this disclosure received financial support from the European Union in the context of Framework Program 7 (FP7/2007-2013) under project No. 241718 EUROBIOREF.

CROSS REFERENCE TO RELATED APPLICATIONS

The present application is a U.S. National Stage Application of International Application No. PCT/FR2012/052778, filed on Dec. 3, 2012, which claims the benefit of French Application No. 1161036, filed on Dec. 1, 2011. The entire contents of each of International Application No. PCT/FR2012/052778 and French Application No. 1161036 are hereby incorporated herein by reference in their entirety.

TECHNICAL FIELD

Embodiments of the disclosure relate to a novel process for synthesizing ω-aminoalkanoic acids which can be used in the polymer industry, in particular polyamides, said process comprising a step of hydroformylation of an unsaturated fatty nitrile.

The term "unsaturated fatty nitrile" is intended to mean any compound of formula (1): $R_1$—CH=CH—[$(CH_2)_q$—CH=CH$]_m$—$(CH_2)_r$—CN in which $R_1$ is H or an alkyl radical comprising from 1 to 11 carbon atoms, comprising, where appropriate, a hydroxyl function, and q, m and r are integer indices such that q=0 or 1, 0≤m≤2 and 4≤r≤13, and mixtures thereof. At the current time, it is known how to produce these unsaturated fatty nitrile compounds from unsaturated fatty acid or ester compounds, or from saturated compounds comprising a hydroxyl function, which may be both of fossil origin and of renewable origin.

For the purposes of the disclosure, the term "ω-aminoalkanoic acids", hereinafter "ω-amino acids" or simply "amino acids", is in fact intended to mean any long-chain ω-amino acid, i.e. in which the chain comprises at least 8 carbon atoms.

Indeed, the polyamides targeted by the embodiments of the disclosure are technical polyamides, i.e. performance polyamides, high performance polyamides, or even very high performance polyamides, produced from monomers comprising at least 8 carbon atoms, preferably at least 10 carbon atoms, as opposed to the "commodity" polyamides, such as "nylon 6", the marketed amounts (volumes) of which are much higher and the costs of which are much lower than those of the technical polyamides.

Known Art:

The polyamide industry uses an entire range of monomers formed from diamines and diacids, from lactams, and especially from ω-amino acids. The latter are defined by the length of the methylene chain (—$CH_2$)$_n$ separating two amide functions —CO—NH—. These monomers are generally produced by chemical synthesis using as the starting materials $C_2$ to $C_4$ olefins, cycloalkanes or benzene, which are hydrocarbons derived from fossil sources. For example, $C_2$ olefins are used to produce the $C_9$ amino acid used in nonanoic acid; $C_4$ olefins are used to produce hexamethylenediamine; laurolactam and caprolactam are produced from cycloalkanes; adipic acid, nylon 6 and nylon 6,6 are produced from benzene.

With regard to the preparation of polyamides from unsaturated nitrile compounds, U.S. Pat. No. 7,026,473 describes the hydroxycarbonylation or the methoxycarbonylation of a pentenenitrile to give 5-cyanovaleric acid or ester (6 C atoms), in the presence of CO (carbon monoxide) and respectively of water or of alcohol. Only the methoxycarbonylation with methanol is in fact exemplified. By means of reduction, the 5-cyanovaleric acid (ester) forms 6-aminocaproic acid (ester), which in turn gives ɛ-caprolactam by cyclization (this is the monomer of nylon-6). The process described in said document has several drawbacks. The methoxycarbonylation step is slow and costly in terms of catalysts. The conversion is not full and requires lengthy reaction times. Furthermore, many co-products are formed, in particular branched products, which must be separated from the linear product that it is desired to produce. Said document does not relate to a process comprising a hydroformylation step, nor to the production of amino acids having a carbon number at least equal to 8. The process described uses nitrile compounds with a short chain, 5 carbons, to produce 6-carbon products with chemical properties very different than those sought by embodiments of the disclosure. Moreover, said document does not relate to the production of biobased amino acids.

Patent document WO 97/33854 describes a process for producing terminal aldehyde by hydroformylation of an alkene, such as hexene, butadiene, methyl 3-pentenoate or 3-pentenenitrile. Said document shows that it is much more difficult to obtain a linear aldehyde (low proportion of linears obtained) from a nitrile (3-pentenenitrile) than from an ester. Furthermore, in the case of hydroformylation, a high proportion (21%, 16.3%) of reduced product (valeronitrile), i.e. no longer containing aldehyde, is obtained from nitrile of the prior art because of the hydrogenation of the double bond by the catalyst. In addition, the obtaining of linear products in the prior art occurs to the detriment of the conversion. Once again, said document does not relate to the production of amino acids having a carbon number at least equal to 8. The process described uses nitrile compounds with a short chain, 5 carbons, to produce 6-carbon products with chemical properties very different than those sought by embodiments of the disclosure. Moreover, said document does not relate to the production of biobased amino acids.

Current developments with regard to the environment are resulting in the use of natural starting materials originating from a renewable source being favored in the fields of energy and chemistry. Only a few monomers are produced at the current time from biobased starting materials, such as castor oil, which makes it possible to produce polyamide 11 sold under the tradename RILSAN®; erucic oil which makes it possible to produce polyamide 13/13, or else lesquerolic oil which makes it possible to produce polyamide 13.

Typically, the process for producing 11-aminoundecanoic acid comprises the following steps:
1) alcoholysis (methanolysis) of castor oil to give methyl ricinoleate (MR),
2) cracking (pyrolysis) of the MR,
3) distillation so as to recover methyl undecylenate,
4) hydrolysis of the methyl undecylenate to give undecylenic acid,
5) hydrobromination so as to obtain 11-bromoundecanoic acid,
6) ammonolysis with an ammoniacal aqueous solution so as to give 11-aminoundecanoic acid.

The polycondensation of the 11-aminoundecanoic acid, by hydrolytic polymerization in the presence of phosphoric acid as catalyst, subsequently makes it possible to obtain polyamide 11.

The process for synthesizing 11-aminoundecanoic acid, carried out industrially for several decades, is satisfactory by and large. However, it has a certain number of drawbacks. The first drawback is that the implementation thereof is in practice subject to access to a single specific starting material, castor oil. Furthermore, the castor bean contains a toxin: ricin, which is extremely toxic. The second drawback is linked to certain reagents used, ammonia and bromine in particular, which require expensive storage and use precautions, and need investment in specific units for separating and recycling the ammonium bromide formed. The third drawback is linked to the co-products obtained via the process: glycerol but also numerous by-products that need to be exploited separately, such as heptanaldehyde, esterol: mixture of uncracked fatty acid esters.

Document U.S. Pat. No. 6,307,108 (see in particular column 9, lines 25-58) describes the production of methyl 12-aminododecanoate from methyl undecylenate (MU), derived from castor oil. The process comprises a step of hydroformylation of the MU so as to form the $C_{12}$ aldehyde ester, and then a step of reductive amination so as to produce the $C_{12}$ amino ester. In order to be able to produce the corresponding amino acid, this process makes it necessary to carry out an additional step of hydrolysis of the amino ester under conditions which have the drawback of leading to its direct polycondensation to "polyamide", the chain growth of which is limited by the presence of the ester groups.

The objective of certain embodiments of the disclosure is therefore to find a novel process for direct synthesis of ω-amino acids, involving other starting materials and reagents, which avoids the formation of by-products, which minimizes the number of steps, and which does not have the abovementioned drawbacks.

The objective of certain embodiments of the disclosure is also to find a novel process for synthesizing the whole range of long-chain ω-amino acids, which is simple to implement, and which as much as possible uses renewable starting materials, which are preferably widely accessible.

The expression "renewable starting materials which are widely accessible" is intended to mean those which are readily available, for example derived from plants which are already grown and/or easy to grow, in an amount compatible with industrial production, and inexpensive.

In this "bio" approach, the applicant has already described several processes for synthesizing ω-amino acids from unsaturated fatty nitriles of renewable origin. Patent documents WO 2010/055273, FR11.55174, FR11.56526 and FR11.57542 describe, in particular, the steps for synthesis of an ⍺-amino acid from an unsaturated fatty nitrile by oxidative cleavage or by cross metathesis with an acrylate resulting in a nitrile acid, and then the hydrogenation thereof to give an amino acid. These processes comprise a metathesis using catalysts and starting co-materials which are relatively expensive, such as acrylonitrile or methyl acrylate. In particular, the ruthenium ligands used to catalyze the metathesis are very specific and constitute most of the costs of the catalyst. Furthermore, on all the carbons of the amino acid formed by means of these processes, at least 2 carbons are not biobased if the methyl acrylate or the acrylonitrile are not themselves biobased, improvement thereof still being sought, the objective being to produce amino acids which aim to be 100% renewable. Moreover, in document WO 2010/055273 in particular, the process comprises a controlled ozonolysis, which amounts to removing a carbon from the carbon chain, whereas, on the contrary, in the case of the synthesis of specialty polyamides, the aim is to increase the length of the carbon chain of the monomers produced. Furthermore, the metathesis process in the abovementioned documents results not in an amino acid, but in an amino ester when the starting materials are, for example, a fatty ester and acrylonitrile, or alternatively a fatty nitrile and methyl acrylate. In order to produce a conventional polyamide, the amino ester must be reconverted beforehand into an amino acid, which requires an additional very complex step to hydrolyze an ester function under hot conditions, without initiating the polymerization of the amino ester.

The objective of certain embodiments of the disclosure is therefore also to find a novel process using catalysts, in particular ligands, and co-materials which are simpler and less expensive, and make it possible to increase the content of material of renewable origin of the amino acids.

The applicant has now found a novel synthesis process involving a step of hydroformylation of an unsaturated fatty nitrile, with hydrogen ($H_2$) and carbon monoxide (CO), and not comprising the abovementioned drawbacks.

DETAILED DESCRIPTION

In the present description, it is specified that, when reference is made to ranges, expressions of the type "ranging from . . . to" or "containing/comprising from . . . to" include the limits of the range. Conversely, expressions of the type "between . . . and . . . " exclude the limits of the range.

Unless otherwise mentioned, the percentages expressed are molar percentages. Unless otherwise mentioned, the parameters to which reference is made are measured at atmospheric pressure.

A subject of certain embodiments of the disclosure is therefore a process for synthesizing an ω-amino acid compound of formula $HOOC—R'—CH_2NH_2$,
where R' is an alkyl radical comprising from 6 to 15 carbon atoms or an alkylene radical comprising from 6 to 15 carbon atoms and from 0 to 2 unsaturations, comprising:

1) a step of hydroformylation of an unsaturated fatty nitrile chosen from the compounds of formula: 
   $R_1—CH=CH—[(CH_2)_q—CH=CH]_m—(CH_2)_r—CN$
   where $R_1$ is H (a hydrogen) or an alkyl radical comprising from 1 to 11 carbon atoms comprising, where appropriate, a hydroxyl function, it being possible for the C=C double bond(s) to be in the cis or trans conformation, q, m and r are integer indices such that q=0 or 1, 0≤m≤2 and 4≤r≤13, and mixtures thereof, by reacting said nitrile with carbon monoxide and dihydrogen so as to obtain at least one fatty nitrile aldehyde of formula:

HOC—R'—CN, 2) a step of oxidation in the presence of dioxygen (molecular oxygen), during which the nitrile aldehyde obtained in step 1 is converted into fatty nitrile acid of formula:

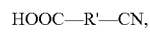
   HOOC—R'—CN, 3) a reduction step during which the nitrile acid obtained in step 2 is converted into an ω-amino acid of formula:

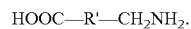
   $HOOC—R'—CH_2NH_2$.

The novel process of an embodiment of the disclosure, in which a step of hydroformylation of an unsaturated fatty nitrile, followed by a step of oxidation of the resulting aldehyde to give an acid, and then by a step of reduction of the nitrile function to give an amine function, is carried out, results in the direct synthesis of amino acids.

Advantageously, the process according to an embodiment of the disclosure also comprises a step of catalytic cross metathesis with an alkene chosen from ethylene, propylene, but-1-ene and but-2-ene, preferably ethylene, propylene and but-1-ene, preferably ethylene or but-1-ene, carried out on the fatty nitrile before step 1) so as to produce an omega-unsaturated fatty nitrile corresponding to the formula:

$R_2$—CH=CH—$(CH_2)_r$—CN, where $R_2$ is H or an alkyl radical comprising from 1 to 3 carbon atoms, preferably corresponding to the formula $CH_2$=CH—$(CH_2)_r$—CN, i.e. preferably when $R_2$ is H.

When $R_2$ is an alkyl radical, during the hydroformylation, the double bond can be brought back to the terminal position, before the addition of the CO, and can therefore result in a linear amino acid, which explains why the various abovementioned alkenes can be used in the process of an embodiment of the disclosure. This step of catalytic cross metathesis with an alkene is conventionally carried out under the same conditions as those described, for example, in patent application WO 2010/055273 on page 9, lines 12 to 18.

The starting unsaturated fatty nitrile used in the process according to an embodiment of the disclosure is generally obtained from unsaturated (or hydroxylated) fatty acid or ester compounds by nitrilation (ammoniation) of at least one acid or ester function of these compounds which can be derived from starting materials of fossil origin or of renewable origin.

The unsaturated fatty acid or ester compounds can be obtained, for example, according to the process described by patent document U.S. Pat. No. 4,510,331. The latter describes in particular the production of 7-octenoic acid, by isomerization of 2,7-octadien-1-ol to give 7-octen-1-al, and then oxidation of the latter to give an acid. The 2,7-octadien-1-ol is produced industrially by reaction ("telomerization") of butadiene with water in the presence of a palladium catalyst according to the process described in patent documents GB 2074156A and DE 3112213. This type of process uses starting materials of fossil origin.

Alternatively, the unsaturated fatty nitriles are produced from unsaturated fatty acids or esters of renewable origin, derived from natural oils. These processes developed recently by Arkema are described in particular in patent documents: WO 2010/055273, FR11.55174, FR11.56526 and FR11.57542.

For the purposes of an embodiment of the disclosure, the term "unsaturated fatty nitrile" is preferably intended to mean those obtained at least partially from unsaturated natural fatty acids. Advantageously, the process according to an embodiment of the disclosure therefore comprises a step of producing said fatty nitrile from an unsaturated fatty acid or ester of natural origin of formula: ($R_1$—CH=CH—[$(CH_2)_q$—CH=CH]$_m$—$(CH_2)_r$—COO—)$_p$—G in which p is an integer index such that $1 \leq p \leq 3$, and G is H (a hydrogen), an alkyl radical having from 1 to 11 carbon atoms or a radical comprising 2 or 3 carbon atoms bearing 1 or 2 hydroxyl function(s), it being possible for the C=C double bond(s) to be in the cis or trans conformation, said production comprising:

the ammoniation (action which consists in introducing ammonia into a product) of the carbonyl function of the unsaturated fatty acid (or ester) of natural origin, to give a nitrile function.

The reaction scheme for the synthesis of nitriles from acids, by ammoniation (or nitrilation, the two terms being used without distinction), well known to those skilled in the art, can be summarized in the following way.

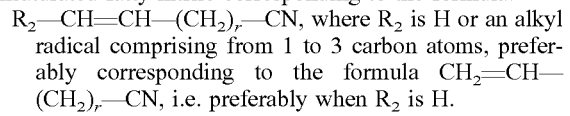

This scheme applies just as much to natural fatty acids (esters) as it does to ω-unsaturated fatty acids. The process can be carried out batchwise in the liquid or gas phase or continuously in the gas phase. The reaction is carried out at a high temperature above 250° C. and in the presence of a catalyst which is generally a metal oxide and most commonly zinc oxide. The continuous removal of the water formed while in addition entraining the ammonia which has not reacted enables rapid completion of the reaction. Liquid-phase ammoniation is very suitable for long fatty chains (comprising at least 10 carbon atoms). However, when operating with shorter chain lengths, gas-phase ammoniation may become more appropriate. It is also known practice, from GB 641 955, to carry out the ammoniation using urea or cyanuric acid as agent. Any other source of ammonia may also be used.

According to one particular embodiment, the unsaturated fatty nitrile used according to an embodiment of the disclosure is produced from natural unsaturated long-chain fatty acids. The term "natural long-chain fatty acid" is intended to mean an acid derived from a plant background or from an animal background, including algae and other microorganisms, and which is therefore renewable, comprising from 6 to 24 carbon atoms, with preferably at least 7 (if the final amino acid has at least 8 C) carbon atoms, preferably at least 8 carbon atoms, preferably at least 10 carbon atoms, and preferably at least 14 carbon atoms per molecule. These various acids are derived from vegetable oils extracted from various plants, such as sunflower, rapeseed, *camelina*, the castor oil plant, *lesquerella*, olive, soya, the palm tree, coriander, celery, dill, carrot, fennel or *Limnanthes alba* (meadowfoam). They are also derived from the terrestrial or marine animal world, and, in the latter case, equally in the form of fish, mammals and algae. It is generally a question of fats originating from ruminants, from fish such as cod, or from marine mammals such as whales or dolphins.

As unsaturated fatty acid suitable more particularly for implementing an embodiment of the disclosure, mention may be made of: petroselenic acid (cis-6-octadecenoic acid), its derivative 6-heptenoic acid obtained by ethenolysis (cross metathesis with ethylene), α-linolenic acid (6,9,12-octadecatrienoic acid), it being possible for these acids to be obtained from coriander for example; cis-8-eicosenoic acid, cis-5,8,11,14-eicosatrienoic acid (arachidonic acid), ricinoleic acid which gives, after dehydration, conjugated 8,10-octadecadienoic acid; caproleic (cis-9-decenoic) acid, palmitoleic (cis-9-hexadecenoic) acid, myristoleic (cis-9-tetradecenoic) acid, oleic (cis-9-octadecenoic) acid, 9-decenoic acid obtained by ethenolysis of an oleic acid for example, elaidic (trans-9-octadecenoic) acid, ricinoleic (12-hydroxy-cis-9-octadecenoic) acid, gadoleic (cis-9-eicosenoic) acid, linoleic (9,12-octadecadienoic) acid, rumenic (9,11-octadecadienoic) acid, conjugated linoleic (9,11-octadecadienoic) acid, it being possible for these acids to be obtained from sunflower, rapeseed, the castor oil plant, olive, soya, the palm tree, flax, avocado, sea buckthorn, coriander, celery, dill, carrot, fennel, *Limnanthes* (meadowfoam); 10,12 conjugated linoleic acid (10,12-octadecadienoic acid), 10-undecylenic acid obtained by thermal cracking of the methyl ester of ricinoleic acid for example;

vaccenic (cis-11-octadecenoic) acid, gondoic (cis-11-eicosenoic) acid, lesquerolic (14-hydroxy-cis-11-eicosenoic) acid, cetoleic (cis-11-docosenoic) acid, which can be obtained from *Lesquerella* oil (lesquerolic), from *Camelina sativa* oil (gondoic), from the oil of a plant of the family Sapindaceae, from fish fat, from oils of microalgae (cetoleic), by dehydration of 12-hydroxystearic acid itself obtained by hydrogenation of ricinoleic acid (vaccenic acid and its trans equivalent), conjugated linoleic acid (9,11-octadecadienoic acid), obtained for example by dehydration of ricinoleic acid; (cis or trans) 12-octadecenoic acid obtained for example by dehydration of 12-hydroxystearic acid (abbreviated as 12HSA), itself obtained by hydrogenation of ricinoleic acid, 10,12 conjugated linoleic acid (10,12-octadecadienoic acid), 12-tridecenoic acid obtained by thermal cracking of the (in particular methyl) ester of lesquerolic acid; erucic (cis-13-docosenoic) acid and brassidic (trans-13-docosenoic) acid which can for example be obtained from erucic rapeseed, from Honesty or from sea kale (sea cabbage); (cis or trans) 13-eicosenoic acid obtained by dehydration of 14-hydroxyeicosanoic acid, itself obtained by hydrogenation of lesquerolic acid, (cis or trans) 14-eicosenoic acid obtained by dehydration of 14-hydroxyeicosanoic acid (abbreviated as 14HEA), itself obtained by hydrogenation of lesquerolic acid (the dehydration can be carried out on both sides of the OH), nervonic (cis-15-tetracosoic) acid which can be obtained from *Malania oleifera* and from Honesty (*Lunaria annua* also known as Pope's coin or moneyplant); or mixtures thereof. It is also possible to dispense with the step of dehydration of the acids 12HSA and 14HEA by carrying out the conversion to nitrile directly on these saturated and hydroxylated fatty acids, as described in the patent document having the filing number FR11.56526. An advantage of this solution is that the hydrogenation of ricinoleic acid in a mixture with the other fatty acids of castor oil results in a mixture no longer containing as majority species only 12HSA, stearic acid and palmitic acid. The dehydration following (or simultaneously with) the conversion into nitrile results in a very clean nitrile containing more than 85% of monounsaturated nitrile. The same is true with 14HEA, as described in patent document FR11.56526.

Among the abovementioned unsaturated fatty acids, preference is given to those which are the most abundantly available, and in particular fatty acids unsaturated in the 6-9 or 5-10 position, the numbering being from the acid group. The use of nitriles and of fatty acids comprising from 10 to 24 carbon atoms, and preferably those comprising 10 carbons or 11 carbons with an unsaturation in the omega or ω position, i.e. at the end of the chain with respect to the acid group, is in fact preferred. Preference is given, for example, to fatty acids containing 18 carbons comprising an unsaturation in the 6-9 or 10 position with respect to the nitrile or acid group, i.e. in the ω-9 or 8 position, respectively, which by ethenolysis will result in ω-unsaturated acids, and also ricinoleic acid which, by thermal cracking of its methyl ester, gives the methyl ester of undecylenic acid.

The fatty acids mentioned above can be isolated by any of the techniques well known to those skilled in the art: molecular distillation, including short path distillation, crystallization, liquid-liquid extraction, complexation with urea, including extraction with supercritical $CO_2$, and/or any combination of these techniques.

According to one particular embodiment of the process of an embodiment of the disclosure, the unsaturated fatty nitrile is obtained from a fatty acid ester, it being possible for the latter to be advantageously chosen from the esters of the abovementioned fatty acids, in particular their methyl esters. The routes for obtaining a fatty nitrile from a fatty acid ester are, for example, described in document WO 2010/089512.

According to another embodiment, the unsaturated fatty nitrile is obtained from a hydroxy fatty acid, such as 12HSA and 14HEA. More generally, the hydroxy fatty acid can advantageously be chosen from those described in the patent application having the filing number FR11.56526.

Alternatively, the unsaturated fatty nitrile is obtained from a triglyceride, it being possible for the latter to be advantageously chosen from: a vegetable oil comprising a mixture of unsaturated fatty acid triglycerides, such as sunflower oil, rapeseed oil, castor oil, *lesquerella* oil, *camelina* oil, olive oil, soya bean oil, palm oil, Sapindaceae (soapberry) oil, in particular avocado oil, sea buckthorn oil, coriander oil, celery oil, dill oil, carrot oil, fennel oil, mango oil, *Limnanthes alba* (meadowfoam) oil, and mixtures thereof; microalgae; animal fats.

According to another embodiment, the unsaturated fatty nitrile is obtained from a plant wax, for example jojoba wax.

Advantageously, the process according to an embodiment of the disclosure also comprises, before the ammoniation step described above:

either a catalytic cross metathesis with ethylene (or other $C_2$ to $C_4$ light alpha-olefin) carried out on the unsaturated fatty acid (or ester or triglyceride) of natural origin, or a pyrolysis of the unsaturated fatty acid or ester of natural origin, followed by distillation (then optionally hydrolysis to give an acid in the case of the ester), so as to produce an omega-unsaturated fatty acid (or ester) of formula: $CH_2=CH-(CH_2)_r-COOR_2$, $R_2$ being H or a $C_1$-$C_4$ alkyl radical, and such that, after the ammoniation step carried out on this omega-unsaturated fatty acid (or ester), an omega-unsaturated fatty nitrile of formula: $CH_2=CH-(CH_2)_r-CN$ is obtained.

The obtaining of such an unsaturated fatty nitrile from an unsaturated fatty acid/ester is in particular described in patent application WO 2010/05527, in particular in the paragraphs describing the "first stage" of the process which is the subject of said document: i.e. on page 5, lines 12 to 32, on page 7, lines 17 to 26, on page 8, lines 1 to 9, on page 10, line 29 to page 11, line 19.

According to one particular embodiment of the process of the disclosure, use is made of an ω-unsaturated nitrile of formula $CH_2=CH-(CH_2)_p-CN$ obtained by conversion of an unsaturated fatty acid/ester in two successive steps (the order being unimportant): ethenolysis (cross metathesis with ethylene) and ammoniation, as described in document WO 2010/055273. According to another variant of the process, hydroxylated fatty acids are used as starting material, such as ricinoleic acid and lesquerolic acid which correspond to the general formula $R_1-CH=CH-(CH_2)_p-COOH$ with $R_1$ equal to $CH_3-(CH_2)_5CHOH-CH_2-$ and p equal, respectively, to 7 and 9. The acid in its methyl ester form is subjected to a pyrolysis resulting in an ω-unsaturated ester of formula $CH_2=CH-(CH_2)_{p+1}-COOCH_3$ which is converted by ammoniation, directly or via the acid, into an ω-unsaturated nitrile. According to yet another embodiment, the unsaturated fatty nitrile is produced as described in document FR11.55174, by ammoniation of a compound of fatty acid, ester or glyceride type, resulting in the corresponding unsaturated nitrile. According to one particular embodiment of the process of the disclosure, the hydrogenation of unsaturated hydroxylated fatty acids comprising at least 18 carbon atoms per molecule, resulting in saturated hydroxylated fatty acids, followed by the dehydration thereof, resulting in monounsaturated fatty acids, are carried out as in the process of document FR11.56526, with, in addition, either an intermediate step of nitrilation of the acid function of the monounsaturated fatty acid, resulting in an unsaturated nitrile, or an intermediate step of nitrilation of the acid function of the saturated hydroxylated fatty acid resulting from the hydrogenation step with concomitant dehydration, resulting in an unsaturated fatty nitrile. Particular conditions for obtaining unsaturated fatty nitriles are described in document FR11.57542, comprising the nitrilation of an ω-unsaturated acid/ester of formula $CH_2=CH-(CH_2)_n-COOR$ in which n is 7 or 8 and R is either H or an alkyl radical comprising 1 to 4 carbon atoms, by reacting ammonia in a reactor operating continuously in the gas phase or in the mixed liquid-gas phase, in the presence of a solid catalyst.

Whether it is a question of metathesis on the fatty nitrile or else on the unsaturated acid (or fatty ester), the cross metathesis reaction with an alkene, such as ethylene, implemented in certain variants of the process of the disclosure, is carried out at a temperature of between 20 and 100° C. at a pressure of 1 to 30 bar, in the presence of a conventional metathesis catalyst, for example of ruthenium type. The reaction time is chosen according to the reagents used and so as to be as close as possible to the equilibrium of the reaction. The reaction is carried out under an alkene pressure.

The pyrolysis reaction implemented in one variant of the process of the disclosure is preferably carried out on the ester form of the fatty acid concerned, generally the methyl ester. The reaction is carried out at high temperature, of between 400 and 750° C. and preferably between 500 and 600° C., in the presence of overheated water vapor.

Preferably, the starting acid is a hydroxylated acid, and it is preferably ricinoleic acid or lesquerolic acid, ricinoleic acid being preferred since it results in 12-aminododecanoic acid according to the process of an embodiment of the disclosure.

According to one preferred embodiment, the process according to an embodiment of the disclosure consists of a process for synthesizing an ω-amino acid compound of formula HOOC—$(CH_2)_{r+2}$—$CH_2NH_2$, from a monounsaturated fatty nitrile compound of formula $CH_2=CH-(CH_2)_r-CN$ comprising the following steps:
the hydroformylation of the unsaturated nitrile compound so as to obtain a nitrile-aldehyde compound of formula HOC—$(CH_2)_{r+2}$—CN, then
the oxidation of the nitrile-aldehyde compound so as to obtain the corresponding nitrile-acid compound of formula HOOC—$(CH_2)_{r+2}$—CN, and the reduction of the nitrile-acid compound to give an ω-amino acid of formula HOOC—$(CH_2)_{r+2}$—$CH_2NH_2$.

1) Hydroformylation

Hydroformylation, also known as oxo process, is a synthesis route for producing aldehydes from alkenes that was discovered in 1938 by Otto Roelen from Ruhrchemie. The basic reaction is the following:

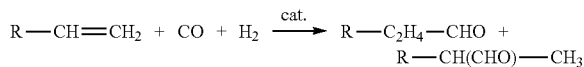

This process is widely used industrially to produce aldehydes in a range of $C_3$-$C_{19}$. Butanal is, moreover, the main product synthesized by this reaction, with approximately 75% of total production using hydroformylation as synthesis route. The hydroformylation step according to the process of an embodiment of the disclosure uses the methods and devices that are well known and already used by conventional hydroformylation processes. All the usual methods for adding and mixing the reagents and the components of a catalyst or catalysts, like the usual separation techniques for the conventional hydroformylation reaction, can therefore be used for this step of the process of an embodiment of the disclosure. The hydroformylation step according to the process of an embodiment of the disclosure has the advantage of being able to be used directly in the numerous devices that exist. This would not be the case with methoxycarbonylation nor with hydroxycarbonylation, for example.

Advantageously, the hydroformylation step is catalyzed in the presence of a catalyst system comprising:
at least one metal of groups V to XI of the periodic table of elements, selected for its activity for converting the unsaturated nitrile, preferably at least one metal of group VIII, preferably at least one metal chosen from rhodium, palladium, cobalt and ruthenium, and mixtures thereof; and
at least one bidentate ligand selected for the selectivity of the hydroformylation reaction in favor of the linear aldehyde, preferably at least one chelating diphosphine, or a monodentate ligand of monophosphine or monophosphite type.

The [ligand]/[metal] molar ratio is advantageously included in the range of from 60:1 to 1:1, preferably from 40:1 to 5:1, preferably from 30:1 to 10:1, preferably from 20:1 to 10:1.

Preferably, the system comprises at least one chelating diphosphine or one monophosphine or monophosphite chosen from: Dppm, Dppe, Dppb, Xantphos, $PPh_3$ and $P(OPh)_3$, preferably Xantphos.

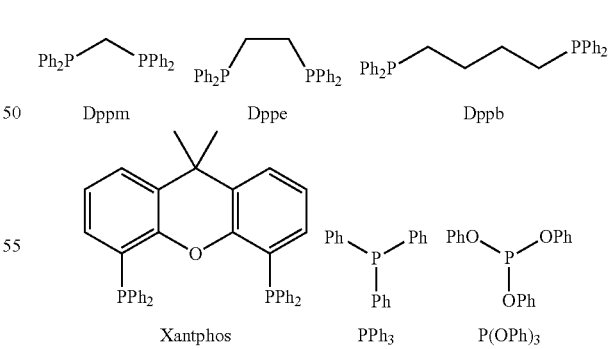

Advantageously, the metal of the system is provided in the form of a precursor comprising said metal and at least one compound chosen from acetylacetonates, halides, carbonyl compounds, and mixtures thereof.

Rhodium-based catalysts are preferred; they substantially improve the conversion. Rhodium catalysts have a better selectivity for aldehydes, cause less hydrogenation as parallel reaction and offer linear product/branched product ratios which are clearly in favor of linear products.

Advantageously, the hydroformylation catalyst system comprises rhodium, preferably provided by means of an Rh(I)-based precursor such as $Rh(acac)(CO)_2$, where acac is an acetylacetonate ligand and CO is a carbonyl ligand, and optionally another metal precursor, such as a ruthenium-based precursor, provided for example in the form $Ru_3(CO)_{12}$. The hydroformylation is preferably catalyzed by a system chosen from: Rh—$PPh_3$, Rh—$P(OPh)_3$ and Rh-Xantphos, and mixtures thereof.

Several strategies make it possible to move a double bond of the unsaturated fatty nitrile into the terminal position where the carbonylation takes place. It is possible to use a double catalyst system, in which a first cobalt or ruthenium catalyst, which isomerizes the internal alkene to terminal alkene, intervenes in parallel with the second rhodium catalyst used for the hydroformylation. According to another embodiment, the presence of methanesulfonic acid (MSA) in addition to the catalyst system used according to an embodiment of the disclosure also makes it possible to orient the double bond in the terminal position. According to another embodiment, a second ligand, in addition to those mentioned above, for example biphephos, is added to the rhodium precursor so as to generate a catalytic species which ensures, in parallel, the dynamic isomerization of the double bond. Thus, the process of an embodiment of the disclosure makes it possible to use nitriles with an internal double bond, and to improve the yields of linear products.

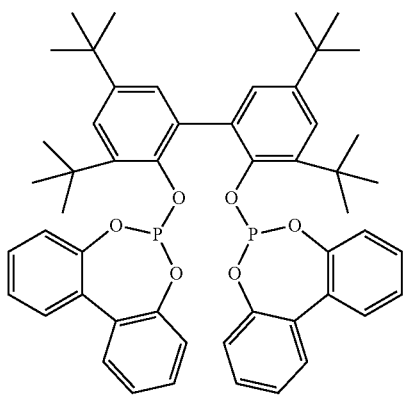

BiPhePhos, MW = 838.94 g/mol

The hydroformylation is preferably carried out in an organic medium, preferably in solution in toluene, but can also be carried out without solvent. The medium may also be aqueous, for example when the process uses propylene during a metathesis step, but there is a risk of a product solubility problem.

According to the process of an embodiment of the disclosure, the hydroformylation is carried out at a temperature included in the range of from 70 to 150° C., preferably from 100 to 140° C., preferably from 120 to 140° C., preferably at a temperature approximately equal to 140° C.

Preferably, the hydroformylation step is carried out for a period of time ranging from 2 to 24 hours, preferably from 2 to 6 hours.

The hydroformylation is preferably carried out at a partial $CO/H_2$ pressure included in the range of from 5 to 50 bar, preferably from 10 to 40 bar, preferably from 10 to 30 bar, preferably at 20 bar of $CO/H_2$ and according to a $CO:H_2$ ratio included in the range of from 1:3 to 3:1, preferably approximately equal to 1:1. It is preferable to avoid using too much $H_2$. A typical syngas has a $CO:H_2$ ratio of from 1:2 to 1:3 when it comes from natural gas, and instead from 2:1 to 1:2 when it comes from biomass. It is particularly advantageous to exploit hydrogen-depleted syngases derived from biomass.

According to the process according to an embodiment of the disclosure, the [Substrate]/[Metal] ratio is advantageously included in the range of from 5000 to 500 000, preferably from 5000 to 400 000, preferably from 5000 to 300 000, preferably from 5000 to 200 000, preferably from 5000 to 150 000.

According to one particular embodiment of the process of an embodiment of the disclosure, the hydroformylation step comprises the recycling of the hydroformylation catalyst system, optionally supplemented by a provision of new (or "fresh") catalyst and/or of new (or "fresh") ligand during a subsequent hydroformylation cycle.

Preferably, the recycled catalyst system is obtained by at least partial evaporation of solvent and/or of nitrile-aldehyde and/or of unreacted reagent contained, for example, in the distillation residue. The catalyst is then recycled to the hydroformylation reactor, with optional addition of phosphine and/or of rhodium and/or flushing of the distillation residue.

2) Oxidation (or Auto-Oxidation, or "Autoxidation")

After the hydroformylation step, the nitrile-aldehyde obtained has the advantage of oxidizing very readily on contact with dioxygen.

According to one preferred embodiment, the oxidation step of the process according to the disclosure is carried out by sparging dioxygen or a dioxygen-containing gas mixture in the product resulting from the hydroformylation, optionally in the presence of the hydroformylation catalyst.

According to one particular embodiment of the disclosure, highly pure dioxygen is used, i.e. dioxygen with a purity greater than 80 mol %, preferably greater than 90 mol %, and even more preferably greater than 99 mol %. Alternatively, air or else dioxygen-enriched air is quite simply used.

Preferably, the oxidation step is carried out without the addition of solvent and/or without the addition of dioxygen activation catalyst. A slight improvement in the yield (an increase of a few yield points is obtained) is observed regarding the aldehydes when traces of alkalines and/or other metals are added as catalyst. Various processes can be used for this oxidation step, and in particular those described in patent documents U.S. Pat. No. 6,680,395, U.S. Pat. No. 6,696,582, U.S. Pat. No. 6,800,783, U.S. Pat. No. 7,138,544, U.S. Pat. No. 7,799,945, WO 10/108586 and FR 2 769 624. According to one particularly advantageous embodiment of the process of the disclosure, the oxidation step is carried out as in document U.S. Pat. No. 6,696,582, without catalyst, in two steps using two successive increasing stationary oxidation temperature phases, in particular for controlling the exothermicity of the reaction. Preferably, the oxidation is carried out in a microreactor, which has the advantage of rapidly evacuating the reaction heat.

When the oxidation step is carried out in the presence of catalyst, use may in particular be made of those described in patent documents U.S. Pat. No. 7,799,945 and U.S. Pat. No. 7,138,544. Typically, an alkaline catalyst (generally in acid salt form) and a co-catalyst taken from group IV to XII of the periodic table are used. The alkalines improve the gas-liquid contact surfaces and, consequently, the migration of the oxygen in the medium. It is the amount of dissolved oxygen which determines the kinetics of the oxidation reaction. The use of these catalysts during the oxidation is not, however, essential. The use of vigorous stirring or of a microreactor is generally sufficient to obtain a very good gas-liquid contact, and therefore a very good exchange of material.

Preferably, the oxidation step is carried out at a partial dioxygen pressure ranging from 1 bar to 50 bar, in particular from 1 bar to 20 bar, preferably from 1 to 5 bar. When the dioxygen is in enriched form (at higher partial pressure than in air), in particular with a purity greater than 80%, the partial pressure of dioxygen injected into the reaction medium is preferably included in the range of from 5 to 20 bar.

Advantageously, the dioxygen is continuously injected into the reaction medium by bubbling, preferably in the form of a stream of air or of dioxygen. This is because dioxygen injected in the form of microbubbles promotes the gas-liquid contact and improves the rate of dissolution in the liquid. The term "microbubbles" is intended to mean bubbles of which the average diameter ranges from 1 μm to 3 mm, preferably 100 μm to 3 mm, preferably from 500 μm to 1 mm. To do this, any dispersion technique may be used: very strong stirring, a self-suction turbine, a Loop® reactor of Buss ChemTech type, a microreactor, a falling film contactor. In the latter case, there may not be microbubbles, since the transfer of material takes place without problem. Use may also be made of a "spinning disk" reactor or a "rotating packed bed" reactor ideal for viscous media.

Advantageously, the molar ratio of the dioxygen relative to the product resulting from the hydroformylation step is included in the range of from 3:2 to 100:2.

It is more practical to speak in terms of molar ratio with respect to the stoichiometry of the oxidation reaction, since the reaction is rapid and exothermic. The reaction is generally stopped when excess dioxygen, representing more than 100% of the stoichiometry, preferably more than 110% of the stoichiometry, preferably more than 120% of the stoichiometry, or even more than 220% of the stoichiometry, has been made to pass through. The molar ratio of the dioxygen relative to the fatty nitrile-acid is thus between (limits excluded) 100% and 5000% of the stoichiometry and preferably greater than 110%.

Advantageously, the oxidation is carried out at a temperature included in the range of from 0° C. to 100° C., preferably from 20° C. to 100° C., in particular from 30° C. to 90° C., preferably from 40° C. to 80° C., optionally in 2 consecutive increasing stationary temperature phases.

3) Reduction or Hydrogenation of the Nitrile Function to Amine

The step of synthesis of the ω-amino fatty esters or ω-amino fatty acids from, respectively, fatty nitrile-esters or fatty nitrile-acids consists of a conventional reduction or hydrogenation. The hydrogenation of the nitrile function automatically leads to the saturation of the double bond present in the molecule. The reduction of the nitrile function to primary amine is well known to those skilled in the art. The hydrogenation is, for example, carried out in the presence of precious metals (Pt, Pd, Rh, Ru, etc.) at a temperature of between 20 and 100° C. under a pressure of from 1 to 100 bar, and preferably from 1 to 50 bar. It can also be carried out in the presence of iron-, nickel- or cobalt-based catalysts, which can lead to more severe conditions with temperatures of about 150° C. and high pressures of several tens of bar. In order to promote the formation of the primary amine, the process is preferably carried out with a partial ammonia pressure. Advantageously, the step of reduction of the fatty nitrile-acids to give ω-amino fatty acids consists of a hydrogenation using any conventional catalyst and preferably Raney nickel and cobalt, in particular Raney nickel optionally deposited on a support such as silica.

Synthesis of Polyamides

According to one advantageous embodiment, the process according to an embodiment of the disclosure also comprises a step of synthesis of polyamide by polymerization using the ω-amino acid obtained in step 3).

Starting from castor oil for example, a methanolysis is carried out so as to obtain the methyl ricinoleate of formula:

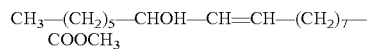
$CH_3-(CH_2)_5-CHOH-CH=CH-(CH_2)_7-COOCH_3$ then thermal cracking is carried out so as to obtain the methyl undecylenate

$CH_2=CH-(CH_2)_8-COOCH_3$ which can be hydrolyzed to give undecylenic acid

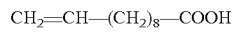
$CH_2=CH-(CH_2)_8-COOH$ then a nitrilation step makes it possible to obtain the undecenenitrile

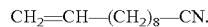
$CH_2=CH-(CH_2)_8-CN.$

Alternatively, the conversion of the methyl ester of undecylenic acid into nitrile is directly carried out.

The resulting undecenenitrile is used in the process of an embodiment of the disclosure according to the following steps:

1) hydroformylation of the nitrile in the presence of CO and of $H_2$, so as to obtain a nitrile-aldehyde comprising 12 carbons:

$HOC-(CH_2)_{10}-CN$ 2) autoxidation of the aldehyde to give an acid, so as to obtain:

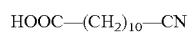
$HOOC-(CH_2)_{10}-CN$ 3) reduction of the nitrile, so as to obtain the $C_{12}$ amino acid

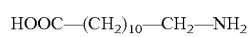
$HOOC-(CH_2)_{10}-CH_2-NH_2$ which makes it possible, by polymerization, to produce polyamide 12 of renewable origin.

Starting from an oil rich in oleic acid (cis-9-octadecenoic acid) of formula $CH_3-(CH_2)_7-CH=CH-(CH_2)_7-COOR,$ the following can be carried out:

ethenolysis (cross metathesis with ethylene or another alpha-olefin), so as to obtain:

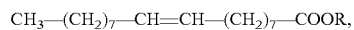
$CH_3-(CH_2)_2-CH=CH_2+CH_2=CH-(CH_2)_7-COOR$ methanolysis and separation of the fatty acids so as to isolate the methyl decenoate $CH_2=CH-(CH_2)_7-COOCH_3$ hydrolysis of the ester to give the acid $CH_2=CH-(CH_2)_2-COOH,$ nitrilation of the acid to give the decenenitrile $CH_2=CH-(CH_2)_2-CN.$

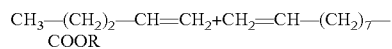

The decenenitrile is then subjected to the following steps according to the process of an embodiment of the disclosure:

hydroformylation of the decenenitrile to give $C_{11}$ nitrile-aldehyde: $HOC-(CH_2)_9-CN,$ autoxidation so as to form the $C_{11}$ nitrile-acid: $HOOC-(CH_2)_9-CN,$ reduction so as to form 11-aminoundecanoic acid HOOC—(CH$_2$)$_9$—CH$_2$—NH$_2$.

Polyamide 11 is produced by polymerization of the 11-aminoundecanoic acid. Alternatively, oleic acid can be converted into oleic nitrile, and then an ethenolysis (or other cross metathesis with an alpha-olefin) can be carried out so as to obtain the nitrile comprising 10 carbon atoms.

By carrying out the process of an embodiment of the disclosure, it is possible to synthesize an entire range of ω-amino acids, and therefore an entire range of polyamides and of polymers.

EXAMPLES

Unless otherwise indicated, all the percentages are percentages by number of moles.

1. Materials

Rh(acac)(CO)$_2$ (sold by Strem) is used as hydroformylation catalyst precursor. The phosphines (sold by Strem) are used as received, or are synthesized.

2. Substrate

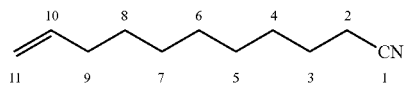

3. Hydroformylation Reaction

General procedure: the hydroformylation reactions are carried out in 30 ml stainless steel autoclaves. Under the typical conditions, a solution, in toluene (10 ml), of Rh(acac) (CO)$_2$ (0.001 mmol), phosphine or diphosphine (0.02 mmol) and undecenenitrile (5.0 mmol) is mixed in a Schlenk tube under an inert argon atmosphere so as to form a homogeneous solution. After stirring at ambient temperature for 1 h, this solution is introduced, via a pipe, into the autoclave preconditioned under an inert atmosphere. The reactor is sealed, flushed several times with a CO/H$_2$ mixture (1:1), then pressurized at 20 bar of this CO/H$_2$ mixture at ambient temperature, and then heated to the desired temperature using a waterbath or an oil bath. The reaction medium is stirred using a magnetic bar. During the reaction, several samples are taken in order to monitor the conversion. After an appropriate reaction time, the autoclave is brought back to ambient temperature and then to atmospheric pressure. The mixture is collected and then analyzed by NMR.

Hydroformylation Products Derived from Undecenenitrile:

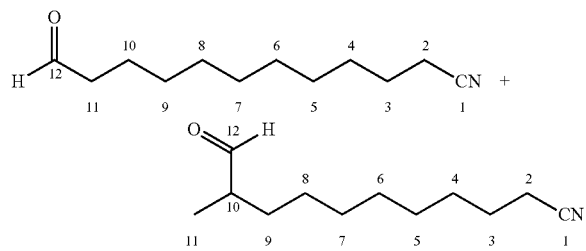

Example 1: Hydroformylation Step According to the Process of an Embodiment of the Disclosure A solution of Rh(acac)(CO)$_2$ (0.25 mg, 0.001 mmol), Xantphos (11.6 mg, 0.02 mmol) and undecenenitrile (826 mg, 5.0 mmol) in toluene (10 ml) is prepared in a Schlenk tube under an inert argon atmosphere so as to form a homogeneous solution which is stirred at ambient temperature for 1 h. The Xantphos/rhodium molar ratio is 20:1 and the substrate/rhodium molar ratio is 5000:1. The solution is introduced, via a pipe, into a 30 ml autoclave preconditioned under an inert atmosphere. The reactor is sealed, flushed several times with a CO/H$_2$ gas mixture (1:1), then pressurized with 20 bar of CO/H$_2$ (1:1) at ambient temperature, and then heated to 120° C. After 2 h, 48% of the undecenenitrile has been consumed. After a reaction time of 12 h, the medium is brought back to ambient temperature and to atmospheric pressure. The mixture is collected and analyzed by NMR. The analysis shows that the conversion of the undecenenitrile is then 99%, and that there remains an internal olefin proportion of 8%, while 92% of products formed correspond to branched (3%) and linear (97%) aldehydes.

Example 2: Hydroformylation Step According to the Process of an Embodiment of the Disclosure A solution of Rh(acac)(CO)$_2$ (0.13 mg, 0.0005 mmol), Xantphos (5.8 mg, 0.01 mmol) and undecenenitrile (826 mg, 5.0 mmol) in toluene (10 ml) is prepared in a Schlenk tube under an inert argon atmosphere so as to form a homogeneous solution which is stirred at ambient temperature for 1 h. The Xantphos/rhodium molar ratio is 20:1 and the substrate/rhodium molar ratio is 10 000:1. The solution is introduced, via a pipe, into a 30 ml autoclave preconditioned under an inert atmosphere. The reactor is sealed, flushed several times with a CO/H$_2$ gas mixture (1:1), then pressurized with 20 bar of CO/H$_2$ (1:1) at ambient temperature, and then heated to 120° C. After 2 h, 25% of the undecenenitrile has been consumed. After a reaction time of 12 h, the medium is brought back to ambient temperature and to atmospheric pressure. The mixture is collected and analyzed by NMR. The analysis shows that the conversion of the undecenenitrile is 99%, and that there remains an internal olefin proportion of 9%, while 91% of products formed correspond to branched (3%) and linear (97%) aldehydes.

Example 3: Hydroformylation Step According to the Process of an Embodiment of the Disclosure A solution of Rh(acac)(CO)$_2$ (0.06 mg, 0.0002 mmol), Xantphos (2.3 mg, 0.004 mmol) and undecenenitrile (826 mg, 5.0 mmol) in toluene (10 ml) is prepared in a Schlenk tube under an inert argon atmosphere so as to form a homogeneous solution which is stirred at ambient temperature for 1 h. The Xantphos/rhodium molar ratio is 20:1 and the substrate/rhodium molar ratio is 20 000:1. The solution is introduced, via a pipe, into a 30 ml autoclave preconditioned under an inert atmosphere. The reactor is sealed, flushed several times with a CO/H$_2$ gas mixture (1:1), then pressurized with 20 bar of CO/H$_2$ (1:1) at ambient temperature, and then heated to 140° C. After 2 h, 22% of the undecenenitrile has been consumed. After a reaction time of 18 h, the medium is brought back to ambient temperature and to atmospheric pressure. The mixture is collected and analyzed by NMR. The analysis shows that the conversion of the undecenenitrile is then 96%, and that there remains an internal olefin proportion of 6%, while 94% of the products formed correspond to branched (4%) and linear (96%) aldehydes.

4. Auto-Oxidation of the Undecenenitrile-Derived Hydroformylation Products

The aldehydes resulting from the undecenenitrile hydroformylation, obtained in examples 1 to 3 above, rapidly oxidize in solution in toluene and on contact with the air (exposure to air in solution in toluene for 24 h at ambient temperature). This finding is confirmed by the disappearance of the aldehyde function carbonyl signal in $^{13}$C NMR at ⊠ 203 ppm and the appearance of a new signal at ⊠ 180 ppm attributable to the carbonyl of the carboxylic acid function.

Reduction of the Auto-Oxidation Products so as to Obtain the C$_{12}$ Amino Acid:

An Ru/SiC catalyst is introduced into a stainless steel autoclave which is equipped with an electromagnetic stirrer and has a capacity of 500 ml. A solution containing 10 g of 11-cyanoundecanoic acid and mixed solvent of 140 ml of n-propanol and 140 ml of aqueous ammonia at 28% by weight of ammonia is introduced into the autoclave. After having flushed the reactor several times with nitrogen, the reactor is pressurized at 35 bar with hydrogen. The reactor is then heated to 110° C. and the stirring and the temperature are kept constant for 1.5 h. The reaction then no longer consumes any hydrogen and the temperature of the autoclave is brought back down to 70° C., and then the pressure is reduced to atmospheric pressure and the colorless liquid is taken off. The solvent is then evaporated off at approximately 60° C. under vacuum, and white crystals (9.7 g) of 12-aminododecanoic acid are recovered.

5. Undecenenitrile Hydroformylation Results 5.1. With Various Catalysts

Several combinations of the precursor Rh(acac)(CO)$_2$ with chelating diphosphines, phosphines or phosphites are studied for the hydroformylation of undecenenitrile in an organic medium. The results are collated in table 1. The conversion of the substrate into a mixture of branched (b) and linear (l) aldehyde is observed with all the catalytic systems:

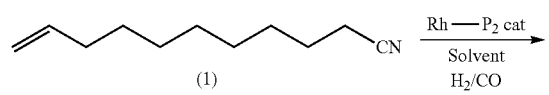

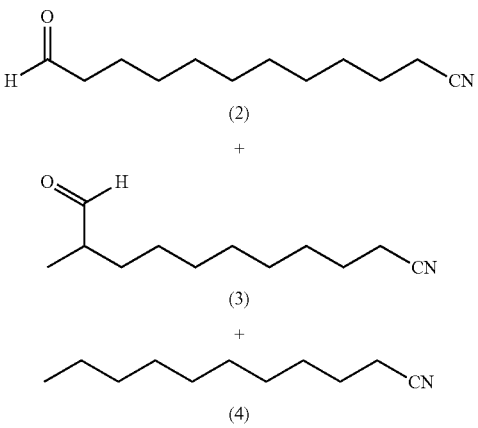

These conversions and also the NI regioselectivity are determined by NMR spectroscopy.

Advantageously, the hydroformylation step of the process according to an embodiment of the disclosure results in a selectivity of at least 95%, preferably of at least 97% of linear aldehydes with respect to the 3 products (2), (3) and (4).

TABLE 1

Hydroformylation of undecenenitrile with various ligands[a]

| Entry | Ligand [L] | Bite angle [L]-[Rh] (°) | Conv. (%)[b] | % internal alkene[c] | Sel. (%)[b] | | |
|---|---|---|---|---|---|---|---|
| | | | | | n-2 | iso-3 | 4 |
| 1 | Dppm | 72 | 5 | 5 | 69 | 31 | nd |
| 2 | Dppe | 85 | 10 | 4 | 46 | 54 | nd |
| 3 | Dppb | 98 | 15 | 4 | 76 | 24 | nd |
| 4 | Xantphos | 107 | 12 | 4 | 97 | 3 | nd |
| 5 | PPh$_3$ | 0 | 85 | 5 | 71 | 29 | nd |
| 6 | P(OPh)$_3$, 20 eq | 0 | 85 | 9 | 68 | 32 | nd |
| 7 | P(OPh)$_3$, 10 eq | 0 | 70 | 8 | 66 | 34 | nd |

[a]Conditions: [olefin] = 0.5M, S/Rh = 5000, L/Rh = 20, 100° C., 20 bar (CO/H$_2$) [1:1], 2 h, toluene (10 ml).
[b]Conversion of the nitrile and selectivity of the aldehydes determined by $^1$H NMR. nd = not detected
[c]% of residual internal alkene or internal alkene formed during the reaction.

As indicated in table 1 above, the Rh—PPh$_3$ and Rh—P(OPh)$_3$ systems exhibit good activity, making it possible to achieve conversions of 85% in 2 h with an amount of catalyst of 0.2 mol % (entries 5-7). The best regioselectivity in favor of the linear aldehyde is observed with the Rh-Xantphos system, which makes it possible to achieve 97% in favor of the linear aldehyde, but with a moderate activity (conversion) at 100° C.

5.2. Influence of the Experimental Conditions

The influence of the experimental conditions on the activity and the selectivity of the hydroformylation reaction is studied. The results are summarized in table 2 below.

TABLE 2

Hydroformylation of undecenenitrile with the Xantphos ligand

| Entry | [S]/[Rh] | Xantphos (eq) | T (° C.) | Time (h) | Conv. (%)[b] | % internal alkene[c] | Sel. (%)[b] n-2 | iso-3 | 4 |
|---|---|---|---|---|---|---|---|---|---|
| 1 | 5000 | 20 | 100 | 2 | 12 | 4 | 97 | 3 | nd |
|   |      |    |     | 24 | 75 | 6 | 97 | 3 |    |
| 2 | 5000 | 20 | 110 | 2 | 26 | 5 | 97 | 3 | nd |
|   |      |    |     | 24 | 99 | 8 | 97 | 3 |    |
| 3 | 5000 | 20 | 120 | 2 | 48 | 6 | 97 | 3 | nd |
|   |      |    |     | 12 | 99 | 8 | 97 | 3 |    |
| 4 | 5000 | 20 | 140 | 2 | 59 | 7 | 97 | 3 | nd |
|   |      |    |     | 4 | 100 | 10 | 97 | 3 |    |
| 5 | 5000 | 10 | 120 | 2 | 48 | 6 | 97 | 3 | nd |
|   |      |    |     | 12 | 99 | 7 | 97 | 3 |    |
| 6 | 10 000 | 20 | 120 | 2 | 25 | 7 | 97 | 3 | nd |
|   |        |    |     | 12 | 98 | 9 | 97 | 3 |    |
| 7 | 10 000 | 10 | 120 | 2 | 21 | 6 | 97 | 3 | nd |
|   |        |    |     | 16 | 99 | 9 | 97 | 3 |    |
| 8 | 20 000 | 20 | 120 | 2 | 5 | 5 | 96 | 4 | nd |
|   |        |    |     | 18 | 98 | 8 | 96 | 4 |    |
| 9 | 20 000 | 20 | 140 | 2 | 22 | 5 | 96 | 4 | nd |
|   |        |    |     | 18 | 96 | 6 | 96 | 4 |    |
| 10 | 40 000 | 20 | 120 | 2 | — | — | 96 | 4 | nd |
|    |        |    |     | 18 | 85 | 8 | 96 | 4 |    |
| 11 | 80 000 | 20 | 110 | 2 | — | — | — | — | nd |
|    |        |    |     | 48 | 99 | 13 | 96 | 4 |    |
| 12 | 100 000 | 20 | 110 | 2 | — | — | — | — |    |
|    |         |    |     | 96 | 99 | 15 | 96 | 4 | nd |

[a]Conditions: [olefin] = 0.5M, L/Rh = 20, 20 bar, CO/H$_2$ [1:1], toluene (10 ml).
[b]Conversion of the nitrile and selectivity of the aldehydes determined by $^1$H NMR; nd =not detected
[c]% of residual internal alkene or internal alkene formed during the reaction.

It is noted that the conversion of the reaction increases logically with the temperature, without affecting the l/b ratio (entries 1-4). There is no marked effect when the ligand/rhodium ratio is reduced (entries 3 and 5). The substrate/rhodium ratio itself clearly affects the reaction in terms of conversion and of percentage of internal alkene formed (entries 3, 6, 8 and 10); typically, the slower the reaction (i.e. the higher the amount of substrate), the more internal alkene originating from the migration of the double bond the residual alkene contains.

For a substrate/rhodium ratio of 100 000, a very high productivity is achieved at 110° C. with a chemoselectivity of 85% and a regioselectivity of 96% in favor of the linear aldehyde (entry 12).

Other Rh-biphephos systems make it possible to achieve high selectivities (>97%) and also good yields in terms of linear aldehyde. The examples below describe tests of undecenenitrile hydroformylation catalyzed by the Rh-biphephos system.

General Procedure:

The hydroformylation reactions were carried out in 30 ml stainless steel autoclaves. Under the typical conditions, a solution, in toluene (10 ml), of Rh(acac)(CO)$_2$ (from 0.001 to 0.0001 mmol), phosphine (from 0.002 to 0.02 mmol) and undecenenitrile (5.0 mmol) is mixed in a Schlenk tube under an inert argon atmosphere so as to form a homogeneous solution. After stirring at ambient temperature for 1 hour, this solution is introduced, via a pipe, into the autoclave preconditioned under an inert atmosphere. The reactor is sealed, flushed several times with a CO/H$_2$ mixture (1:1), then pressurized at 20 bar of this CO/H$_2$ mixture at ambient temperature, and then heated to the desired temperature using a waterbath or an oil bath. During the reaction, several samples are taken in order to monitor the conversion. After an appropriate reaction time, the autoclave is brought back to ambient temperature and then to atmospheric pressure. The mixture is collected and then analyzed by NMR.

TABLE 3

Effect of temperature during the undecenenitrile hydroformylation[a]

| Entry | Temp (° C.) | Conv.[b] (%) | Internal alkenes (%)[c] | Sel. (%)[b] 2 | 3 |
|---|---|---|---|---|---|
| 1 | 80 | 52 | 20 | 99 | 1 |
| 2 | 100 | 75 | 20 | 99 | 1 |
| 3 | 120 | 88 | 22 | 99 | 1 |
| 4 | 140 | 94 | 26 | 99 | 1 |

[a][undecenenitrile] = 5.0 mmol, [undecenenitrile]/[Rh] = 20 000, [biphephos]/[Rh] = 20, toluene = 10 ml, P = 20 bar CO/H$_2$ (1:1), 4 h.
[b]Conversion of the nitrile/selectivity/% of internal alkene and 2 and 3 determined by $^1$H NMR and GLC analyses.
[c]% of internal alkene, residual or formed during the reaction.

The previous examples show that the Rh-biphephos system is very active and selective in undecenenitrile hydroformylation (table 3). In a temperature range of 80-120° C., good conversions (52-94% of 20 000 equiv) were obtained in 4 h, and also excellent selectivities ranging up to 99%.

In order to overcome the possible problem of isomerization leading to the formation of internal alkenes, other experiments are carried out while increasing the reaction time, since, after total conversion of the substrate, the catalyst can isomerize the internal alkenes to terminal alkene and hydroformylize the latter to linear aldehyde (table 4).

Example of Table 4, Entry 4: Hydroformylation of 1,10-Undecenenitrile (Rh-Biphephos) with S/Rh=20 000 and L/Rh=20 and Recycling of the Catalyst:

A solution, in toluene, of Rh(acac)(CO)$_2$ (0.65 mg, 0.0025 mmol), biphephos (4 mg, 0.005 mmol) and undecenenitrile (826 mg, 5.0 mmol) is prepared in a Schlenk tube under an inert argon atmosphere so as to form a homogeneous solution which is stirred at ambient temperature for 1 h. The biphephos/rhodium molar ratio is 20:1 and the substrate/rhodium molar ratio is 20 000:1. The solution is introduced, via a pipe, into a 30 ml autoclave preconditioned under an inert atmosphere. The reactor is sealed, flushed several times with a $CO/H_2$ gas mixture (1:1), then pressurized with 20 bar of $CO/H_2$ (1:1) at ambient temperature, and then heated to 120° C. After 4 h, 67% of the undecenenitrile has been consumed. After 24 h, the medium is brought back to ambient temperature and to atmospheric pressure. The mixture is collected and analyzed by NMR. The analysis shows that the reaction is complete and that there remains an internal olefin proportion of 13%, while 87% of products formed correspond to branched (1%) and linear (99%) aldehydes. If the reaction is allowed to continue, the internal alkenes will be isomerized and hydroformylized.

Thus, after 48 h of reaction, there then remains only a 5% proportion of internal olefins, while 95% of products formed correspond to branched (1%) and linear (99%) aldehydes.

Once the reaction has finished, recycling by distillation is carried out, under an inert atmosphere, using a Kugelrohr ("ball oven") distillation system at a temperature of 180° C. and a pressure of 1 mbar. The hydroformylation products obtained in a first fraction are stable and no trace of residual catalyst or ligand was detected after NMR analysis CH and $^{31}P$). The catalyst contained at the bottom of the column was reused for a second run. For this, the catalyst is reintroduced into the Schlenk tube with 10 ml of toluene, a new amount of biphephos (0.0005 mmol, 5 equiv) and 5 mmol of 1,10-undecenenitrile. The solution is again introduced, via a pipe, into a 30 ml autoclave preconditioned under an inert atmosphere. The reactor is sealed, flushed several times with a $CO/H_2$ gas mixture (1:1), then pressurized with 20 bar of $CO/H_2$ (1:1) at ambient temperature, and then heated to 120° C. After 48 h, the medium is then brought back to ambient temperature and to atmospheric pressure. The mixture is collected and analyzed by NMR. The analysis shows that the reaction is complete and that there remains a 2% proportion of internal olefin, while 98% of products formed correspond to branched (2%) and linear (98%) aldehydes. This recycling can be carried out on several cycles without loss of selectivity.

Example of Table 4, Entry 7: Hydroformylation of 1,10-Undecenenitrile (Rh-Biphephos) with S/Rh=50 000 and L/Rh=20:

A solution, in toluene (0.65 mg, 0.0025 mmol), of $Rh(acac)(CO)_2$, biphephos (2.0 mg, 0.0025 mmol) and undecenenitrile (826 mg, 5.0 mmol) is prepared in a Schlenk tube under an inert argon atmosphere so as to form a homogeneous solution which is stirred at ambient temperature for 1 h. The biphephos/rhodium molar ratio is 10:1 and the substrate/rhodium molar ratio is 20 000:1. The solution is introduced, via a pipe, into a 30 ml autoclave preconditioned under an inert atmosphere. The reactor is sealed, flushed several times with a $CO/H_2$ gas mixture (1:1), then pressurized with 20 bar of $CO/H_2$ (1:1) at ambient temperature, and then heated to 120° C. After 48 h, the medium is brought back to ambient temperature and to atmospheric pressure. The mixture is collected and analyzed by NMR. The analysis shows that the reaction is complete and that there remains an 18% proportion of internal olefin, while 82% of products formed correspond to branched (2%) and linear (98%) aldehydes. If the reaction is allowed to continue, the internal alkenes will be isomerized and hydroformylized.

TABLE 4

| Entry | [S]/[Rh] | Biphephos (equiv) | Time (h) | Conv. (%)[b] | Internal alkenes (%)[c] | Sel. (%)[b] | | | Internal aldehydes |
|---|---|---|---|---|---|---|---|---|---|
| | | | | | | n-2 | iso-3 | 4 | |
| 1 | 10 000 | 20 | 4 | 65 | 28 | 99 | 1 | nd | — |
| | | | 24 | 100 | 12 | 99 | 1 | nd | — |
| 2 | 10 000 | 5 | 4 | 63 | 42 | 99 | 1 | nd | — |
| | | | 24 | 100 | 14 | 99 | 1 | nd | — |
| 3 | 10 000 | 2 | 4 | 58 | 38 | 99 | 1 | nd | — |
| | | | 24 | 100 | 9 | 90 | 4 | nd | 6 |
| 4 | 20 000 | 20 | 4 | 67 | 20 | 99 | 1 | nd | — |
| | | | 24 | 99 | 13 | 99 | 1 | nd | — |
| | | | 48 | 100 | 7 | 99 | 1 | nd | — |
| | | | 72 | 100 | 4 | 99 | 1 | nd | — |
| 5 | 20 000 | 10 | 4 | 81 | 21 | 99 | 1 | nd | — |
| | | | 24 | 99 | 12 | 99 | 1 | nd | — |
| | | | 48 | 100 | 6 | 99 | 1 | nd | — |
| | | | 72 | 100 | 4 | 99 | 1 | nd | — |
| 6 | 20 000 | 5 | 4 | 73 | 23 | 99 | 1 | nd | — |
| | | | 24 | 99 | 17 | 99 | 1 | nd | — |
| | | | 48 | 100 | 11 | 99 | 1 | nd | — |
| | | | 72 | 100 | 6 | 99 | 1 | nd | — |
| 7 | 50 000 | 20 | 4 | 48 | 13 | 99 | 1 | nd | — |
| | | | 72 | 100 | 19 | 99 | 1 | nd | — |
| 8 | 50 000 | 5 | 4 | 65 | 25 | 99 | 1 | nd | — |
| | | | 48 | 100 | 18 | 99 | 1 | nd | — |
| 9 | 100 000 | 20 | 4 | 5 | 16 | 99 | 1 | nd | — |
| | | | 72 | 96 | 27 | 99 | 1 | nd | — |
| 10 | 100 000 | 10 | 4 | 3 | 8 | 99 | 1 | nd | — |
| | | | 24 | 99 | 24 | 98 | 2 | nd | — |
| | | | 96 | 100 | 12 | 92 | 4 | nd | 4 |
| 11 | 100 000 | 5 | 4 | 5 | 8 | 99 | 1 | nd | — |

TABLE 4-continued

| Entry | [S]/[Rh] | Biphephos (equiv) | Time (h) | Conv. (%)[b] | Internal alkenes (%)[c] | Sel. (%)[b] | | | Internal aldehydes |
|---|---|---|---|---|---|---|---|---|---|
| | | | | | | n-2 | iso-3 | 4 | |
| | | | 24 | 99 | 45 | 92 | 6 | nd | 2 |
| | | | 96 | 100 | 28 | 86 | 8 | nd | 6 |

[a][undecenenitrile] = 5.0 mmol, [undecenenitrile]/[Rh] = 20 000, [biphephos]/[Rh] = 20, toluene = 10 ml, P = 20 bar CO/H$_2$ (1:1), 4 h.
[b]of the nitrile/selectivity/% of internal alkene and 2 and 3 determined by $^1$H NMR and GLC analyses.
[c]% of internal alkene, residual or formed during the reaction.
nd = not detected.

The Rh-biphephos catalyst can also be recycled by distilling the solvent and the organic products (aldehydes, residual internal alkenes) with a Kugelrohr ("ball oven") system, at 180° C. under a dynamic vacuum of 1 mbar. The solid residue (still with a small amount of organic products) thus recovered can then be reused on several cycles without substantial loss of selectivity, after having occasionally added fresh ligand between two cycles so as to prevent a modification of the active species in catalysis. This procedure is first carried out using an S/Rh ratio of 20 000 and an L/Rh ratio of 10 (table 5). Thus, very good selectivities were obtained on 4 cycles and the isomerization/hydroformylation of the internal alkenes appears to be just as efficient since there was no accumulation of these internal alkenes.

neous solution which is stirred at ambient temperature for 1 h. The biphephos/rhodium molar ratio is 20:1 and the substrate/rhodium molar ratio is 100 000:1. The solution is introduced, via a pipe, into a 30 ml autoclave preconditioned under an inert atmosphere. The reactor is sealed, flushed several times with a CO/H$_2$ gas mixture (1:1), then pressurized with 20 bar of CO/H$_2$ (1:1) at ambient temperature, and then heated to 120° C. After 48 h, 85% of the undecenenitrile has been consumed. The temperature is then adjusted to 130° C., over the course of a further 48 h reaction time, and the medium is brought back to ambient temperature and to atmospheric pressure. The mixture is collected and analyzed by NMR. The analysis shows that the reaction is complete

TABLE 5

Hydroformylation of undecenenitrile during 4 cycles[a]

| Entry[a] | Cycle | biphephos added (eq) | T (° C.) | Time (h) | Conv. (%)[b] | Internal alkenes (%)[c] | Sel. (%)[b] | | internal aldehydes |
|---|---|---|---|---|---|---|---|---|---|
| | | | | | | | n-2 | iso-3 | |
| 1 | I | — | 120 | 24 | 95 | 11 | 99 | 1 | 0 |
| | | | 130 | 48 | 100 | 5 | 99 | 1 | 0 |
| 2[d] | II | 5 | 120 | 24 | 40 | 12 | 99 | 1 | 0 |
| | | | 130 | 48 | 100 | 2 | 98 | 2 | 0 |
| 3[d] | III | 5 | 120 | 24 | 35 | 20 | 98 | 2 | 0 |
| | | | 130 | 48 | 100 | 6 | 98 | 2 | 0 |
| 4[e] | IV | — | 120 | 24 | 26 | 11 | 99 | 1 | 0 |
| | | | 130 | 48 | 90 | 9 | 97 | 3 | 0 |

[a][undecenenitrile] = 10 mmol, [undecenenitrile]/[Rh] = 20 000, [biphephos]/[Rh] = 10, toluene = 5 ml, P = 20 bar CO/H$_2$ (1:1).
[b]Conversion of the nitrile/selectivity/% of internal alkene and 2 and 3 determined by $^1$H NMR and GLC analyses.
[c]% of internal alkene, residual or formed during the reaction.
nd = not detected.
[d]The catalyst is recycled under an inert atmosphere, 5 equiv of biphephos were added, toluene = 5 ml, P = 20 bar CO/H$_2$ (1:1).
[e]The catalyst is recycled under an inert atmosphere, and reused without addition of ligand, toluene = 5 ml, P = 20 bar CO/H$_2$ (1:1).

These results prove that it is easy, according to the process of an embodiment of the disclosure, to recycle this catalyst via the distillation route. Other tests are carried out while increasing the S/Rh ratio to 100 000 with a higher L/Rh ratio (initially 20). Table 6 shows that this procedure operates without any great reduction in activity; the productivity is very good since it reaches close to 200 000 on two cycles (the first+the recycling), while using only 25 equivalents of biphephos.

Examples of Table 6, Entries 1 and 2: Hydroformylation of 1,10-Undecenenitrile (Rh-Biphephos) with S/Rh=100 000 and L/Rh=20; and Recycling of the Catalyst:

A solution, in toluene (0.026 mg, 0.0001 mmol), of Rh(acac)(CO)$_2$, biphephos (1.6 mg, 0.002 mmol) and undecenenitrile (1.65 g, 10.0 mmol) is prepared in a Schlenk tube under an inert argon atmosphere so as to form a homogeand that there remains a 9% proportion of internal olefin, while 91% of products formed correspond to branched (2%) and linear (98%) aldehydes.

Once the reaction has finished, recycling by distillation is carried out, under an inert atmosphere, using a Kugelrohr distillation system at a temperature of 180° C. and a dynamic vacuum of 1 mbar. The hydroformylation products obtained in a first fraction are stable and no trace of residual catalyst or ligand is detected after NMR analysis CH and $^{31}$P). The catalyst contained at the bottom of the column is reused for a second run. For this, the catalyst is reintroduced into the Schlenk tube with 10 ml of toluene, a fresh amount of biphephos (0.5 mol, 5 equiv) and 10 mmol of 1,10-undecenenitrile. The solution is again introduced, via a pipe, into a 30 ml autoclave preconditioned under an inert atmosphere. The reactor is sealed, flushed several times with a CO/H$_2$ gas mixture (1:1), then pressurized with 20 bar of CO/H$_2$ (1:1) at ambient temperature, and then heated to 120° C. After 48 h, 72% of the undecenenitrile is consumed. The temperature is then adjusted to 130° C., over the course of a further 48 h reaction time, and the medium is brought back to ambient temperature and to atmospheric pressure. The mixture is collected and analyzed by NMR. The analysis shows that the reaction is complete and that there remains an 11% proportion of internal olefins, while 89% of the products formed correspond to branched (2%) and linear (98%) aldehydes.

TABLE 6

Hydroformylation of undecenenitrile on 2 cycles at high S/Rh ratios[a]

| Entry[a] | Cycle | Biphephos added (eq) | T (° C.) | Time (h) | Conv. (%)[b] | % internal alkenes[c] | Sel. (%)[b] | | |
|---|---|---|---|---|---|---|---|---|---|
| | | | | | | | n-2 | iso-3 | ss-pdt |
| 1 | Cycle I | — | 120 | 48 | 85 | 23 | 99 | 1 | — |
| | | | 130 | 96 | 100 | 9 | 98 | 2 | — |
| 2[d] | Cycle II | 5 | 120 | 48 | 72 | 24 | 99 | 1 | — |
| | | | 130 | 96 | 100 | 11 | 98 | 2 | — |

[a][undecenenitrile] = 10 mmol, [undecenenitrile]/[Rh] = 100 000, [biphephos]/[Rh] = 20, toluene = 10 ml, P = 20 bar CO/H$_2$ (1:1).
[b]Conversion of the nitrile/selectivity/% of internal alkene determined by $^1$H NMR and GLC analyses.
[c]% of internal alkene, residual or formed during the reaction.
[d]The catalyst is recycled under an inert atmosphere, 5 equiv of biphephos were added, toluene = 10 ml, P = 20 bar CO/H$_2$ (1:1).

Comparative Example with Methyl 10-Undecenoate

Other tests are carried out in order to compare the performance levels of the Rh-biphephos system on undecenenitrile and methyl 10-undecenoate (table 7). The tests are carried out with methyl undecenoate which was distilled beforehand. In the light of the results (in particular when comparing entry 4 of table 7 with entry 1 of table 6), it appears that the Rh-biphephos system is less selective and less active with respect to methyl 10-undecenoate than with the fatty nitrile.
Example of Table 7, Entry 4: Hydroformylation of Methyl 10-Undecenoate (Rh-Biphephos) with S/Rh=100 000 and L/Rh=20:

This test is carried out under the same conditions as those described above in the example of table 6, with the 1,10-undecenenitrile being replaced with methyl 10-undecenoate. There is no recycling of the catalyst in this case. After 48 h, 68% of the methyl 10-undecenoate has been consumed. A sample is collected and analyzed by NMR. The analysis shows that there remains a 45% proportion of internal olefin, while 23% of products formed correspond to branched (15%) and linear (85%) aldehydes.

TABLE 7

Hydroformylation of methyl 10-undecenoate[a]

| Entry | S/Rh | L/Rh | T (° C.) | Time (h) | Conv. (%)[b] | % internal alkenes[c] | Sel. (%)[b] | | |
|---|---|---|---|---|---|---|---|---|---|
| | | | | | | | n-2 | iso-3 | ss-pdt |
| 1 | 2000 | 10 | 100 | 24 | 100 | 10 | 96 | 4 | — |
| 2 | 5000 | 10 | 120 | 24 | 100 | 15 | 95 | 3 | 2 |
| 3 | 20 000 | 10 | 120 | 48 | 93 | 12 | 90 | 5 | 5 |
| 4 | 100 000 | 20 | 120 | 48 | 68 | 45 | 85 | 12 | 3 |

[a]distilled methyl 10-undecenitrile = 5.0 mmol, toluene = 10 ml, P = 20 bar CO/H$_2$ (1:1).
[b]Conversion of the methyl 10-undecenoate/selectivity/% of internal alkene determined by $^1$H NMR and GLC analyses.
[c]% of internal alkene, residual or formed during the reaction.

When all is said and done, the process according to an embodiment of the disclosure has numerous advantages compared with the existing processes. It is simple to implement. It does not require any particular equipment and can be implemented in existing industrial devices, which makes it possible to initiate marketing, even with small tonnages in terms of production capacity. It also does not require expensive starting materials or expensive catalysts. The process according to an embodiment of the disclosure is versatile since it makes it possible to use a wide range of starting materials; it is not linked to one oil in particular.

Contrary to the prior art processes which necessarily use a metathesis step, and result in an amino ester when the starting materials are, for example, a fatty ester and acrylonitrile, or a fatty nitrile and methyl acrylate, an amino acid is obtained according to the process of an embodiment of the disclosure. Furthermore, the number of carbons of non-renewable origin of the amino acid obtained according to the process of an embodiment of the disclosure is zero, or is limited to 1 when the syngas (CO) used during the hydroformylation is not produced from biomass.

The invention claimed is:

1. A process for synthesizing an ω-amino acid compound of formula

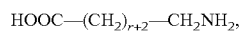
HOOC—(CH$_2$)$_{r+2}$—CH$_2$NH$_2$, wherein r is an integer wherein 4≤r≤13 from a monounsaturated fatty nitrile compound of formula

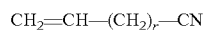
CH$_2$=CH—(CH$_2$)$_r$—CN the process comprising:
1) a step of hydroformylation of the monounsaturated fatty nitrile compound by reacting said nitrile with carbon monoxide and dihydrogen to obtain a nitrile aldehyde compound of formula HOC—(CH$_2$)$_{r+2}$—CN, then
2) a step of oxidation, in the presence of dioxygen, of the nitrile aldehyde compound to obtain a corresponding nitrile acid compound of formula HOOC—(CH$_2$)$_{r+2}$—CN, and
3) a step of reduction of the nitrile acid compound to give an ω-amino acid of formula

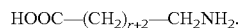
HOOC—(CH$_2$)$_{r+2}$—CH$_2$NH$_2$.

2. The process as claimed in claim 1, wherein the hydroformylation is catalyzed in the presence of a catalyst system comprising:
at least one metal of groups V to XI of the periodic table of elements, selected for its nitrile conversion activity; and at least one bidentate or monodentate ligand selected for the selectivity of the hydroformylation reaction in favor of the linear aldehyde.

3. The process as claimed in claim 2, wherein the catalyst system comprises at least one phosphine, one phosphite or one chelating diphosphine selected from the group consisting of $PPh_3$, $P(OPh)_3$, Dppm, Dppe, Dppb and Xantphos.

4. The process as claimed in claim 2, wherein the metal of the catalyst system is provided in the form of a precursor comprising said metal and at least one compound selected from the group consisting of acetylacetonates, carbonyl compounds, and mixtures thereof.

5. The process as claimed in claim 2, wherein the hydroformylation catalyst system comprises rhodium, and/or ruthenium.

6. The process as claimed in claim 2, wherein the hydroformylation is catalyzed by a catalyst system selected from the group consisting of $Rh$—$PPh_3$, $Rh$—$P(OPh)_3$ and Rh-Xantphos, and mixtures thereof.

7. The process as claimed in claim 2, wherein the [ligand]/[metal] molar ratio is included in the range of from 60:1 to 1:1.

8. The process as claimed in claim 1, wherein the hydroformylation is carried out in an organic medium.

9. The process as claimed in claim 1, wherein the hydroformylation is carried out at a temperature included in the range of from 70 to 150° C.

10. The process as claimed in claim 1, wherein the hydroformylation is carried out for a period of time ranging from 2 to 24 hours.

11. The process as claimed in claim 1, wherein the hydroformylation is carried out at a partial $CO/H_2$ pressure included in the range of from 5 to 50 bar and according to a $CO:H_2$ ratio included in the range of from 1:3 to 3:1.

12. The process as claimed in claim 1, wherein the [Substrate]/[Metal] ratio is included in the range of from 5000 to 500 000.

13. The process as claimed in claim 1, wherein the oxidation step is carried out by sparging dioxygen or a dioxygen-containing gas mixture in the product resulting from the hydroformylation, optionally in the presence of the hydroformylation catalyst.

14. The process as claimed in claim 1, wherein the oxidation step is carried out without the addition of solvent and/or without the addition of dioxygen activation catalyst.

15. The process as claimed in claim 1, wherein the oxidation step is carried out at a partial dioxygen pressure ranging from 1 bar to 50 bar.

16. The process as claimed in claim 1, wherein the dioxygen is continuously injected into the reaction medium by bubbling.

17. The process as claimed in claim 1, wherein a molar ratio of the dioxygen relative to the product resulting from the hydroformylation step is included in the range of from 3:2 to 100:2.

18. The process as claimed in claim 1, wherein the oxidation is carried out at a temperature included in the range of from 0° C. to 100° C., optionally in 2 consecutive increasing stationary temperature phases.

19. The process as claimed in claim 2, wherein the hydroformylation step comprises the recycling of the hydroformylation catalyst system, optionally supplemented by a provision of new catalyst and/or ligand during a subsequent hydroformylation cycle.

20. The process as claimed in claim 19, wherein the recycled catalyst system is obtained by at least partial evaporation of solvent and/or of nitrile-aldehyde and/or of unreacted reagent.

21. The process as claimed in claim 1, wherein the hydroformylation step results in a selectivity of at least 95% of linear aldehydes.

22. The process as claimed in claim 1, also comprising a step of catalytic cross metathesis with an alkene selected from the group consisting of ethylene, propylene, but-1-ene and but-2-ene, carried out on a unsaturated fatty nitrile before step 1) R2-CH to produce the monounsaturated fatty nitrile compound of formula $CH_2$=$CH$—$(CH_2)_r$—$CN$.

\* \* \* \* \*

UNITED STATES PATENT AND TRADEMARK OFFICE
CERTIFICATE OF CORRECTION

PATENT NO.          : 10,125,221 B2
APPLICATION NO.     : 14/362309
DATED               : November 13, 2018
INVENTOR(S)         : Jean-Luc Dubois et al.

Page 1 of 1

It is certified that error appears in the above-identified patent and that said Letters Patent is hereby corrected as shown below:

In the Specification

Column 2, Line 9: change "?-caprolactam" to --ε-caprolactam--

Column 3, Line 53: change "?-amino acid" to --ω-amino acid--

Column 9, Line 60: change "?-amino acid" to --ω-amino acid--

Column 14, Line 10: change "?-amino acid" to --ω-amino acid--

Column 15, Line 9: change "?-amino acids" to --ω-amino acids--

Column 17, Line 25-27: change "? 203 ppm and the appearance of a new signal at ? 180 ppm attributable to the carbonyl of the carboxylic acid function." to --δ 203 ppm and the appearance of a new signal at δ 180 ppm attributable to the carbonyl of the carboxylic acid function.--

Column 24, Line 64: change "0.5 ? mol, 5 equiv" to --0.5 ☐mol, 5 equiv--

Signed and Sealed this
First Day of September, 2020

Andrei Iancu
*Director of the United States Patent and Trademark Office*